United States Patent [19]
Gillies et al.

[11] Patent Number: 5,356,402
[45] Date of Patent: * Oct. 18, 1994

[54] REUSABLE DIAPER

[76] Inventors: Suzanne Gillies; John Gillies, both of R.R. #3, King City, Ontario, Canada

[*] Notice: The portion of the term of this patent subsequent to Dec. 7, 2010 has been disclaimed.

[21] Appl. No.: 54,474

[22] Filed: Apr. 30, 1993

Related U.S. Application Data

[63] Continuation-in-part of Ser. No. 650,543, Feb. 5, 1991, Pat. No. 5,267,991.

[30] Foreign Application Priority Data

Sep. 7, 1990 [GB] United Kingdom ............... 9019619.7

[51] Int. Cl.$^5$ ............................................ A61F 13/15
[52] U.S. Cl. .................... 604/375; 604/378; 604/380; 604/384; 604/385.1; 604/386; 604/387
[58] Field of Search ............... 604/367, 377, 383, 386, 604/372, 375, 366, 380, 384, 393, 381, 385.1, 385.2, 386, 387, 364; 428/102; 66/190-192, 195-196, 175

[56] References Cited

U.S. PATENT DOCUMENTS

| | | | |
|---|---|---|---|
| Re. 30,972 | 6/1982 | Kyle et al. ............... | 604/383 |
| 3,397,697 | 8/1968 | Rickard ................ | 604/387 |
| 3,717,150 | 2/1973 | Schwartz .............. | 604/383 |
| 4,144,612 | 3/1979 | Yamaguchi .......... | 428/102 |

FOREIGN PATENT DOCUMENTS 8901062 2/1989 PCT Int'l Appl. ............... 604/367

Primary Examiner—Randall L. Green
Assistant Examiner—K. M. Reichle
Attorney, Agent, or Firm—Jeffrey T. Imai; Arne I. Fors; D. Doak Horne

[57] ABSTRACT

A reusable pad for the absorption, dispersion and retention of a liquid comprises an interior layer of hydrophobic material for receiving the liquid, a median layer consisting of a non-woven web of carded and cross-laid viscose rayon fibres and an outer layer of substantially waterproof polyurethane film. The fibres of the median layer have a cross-section of substantially rigid multilimbed configuration. The web is stitchbonded to form a cohesive layer for dispersing and absorbing the liquid. The web is stitchbonded with a thread under medium tension whereby uniform absorption characteristics are retained throughout said web. The interior layer, median layer and outer layer are joined to form a pad of unitary construction and capable of being washed for reuse.

20 Claims, 5 Drawing Sheets

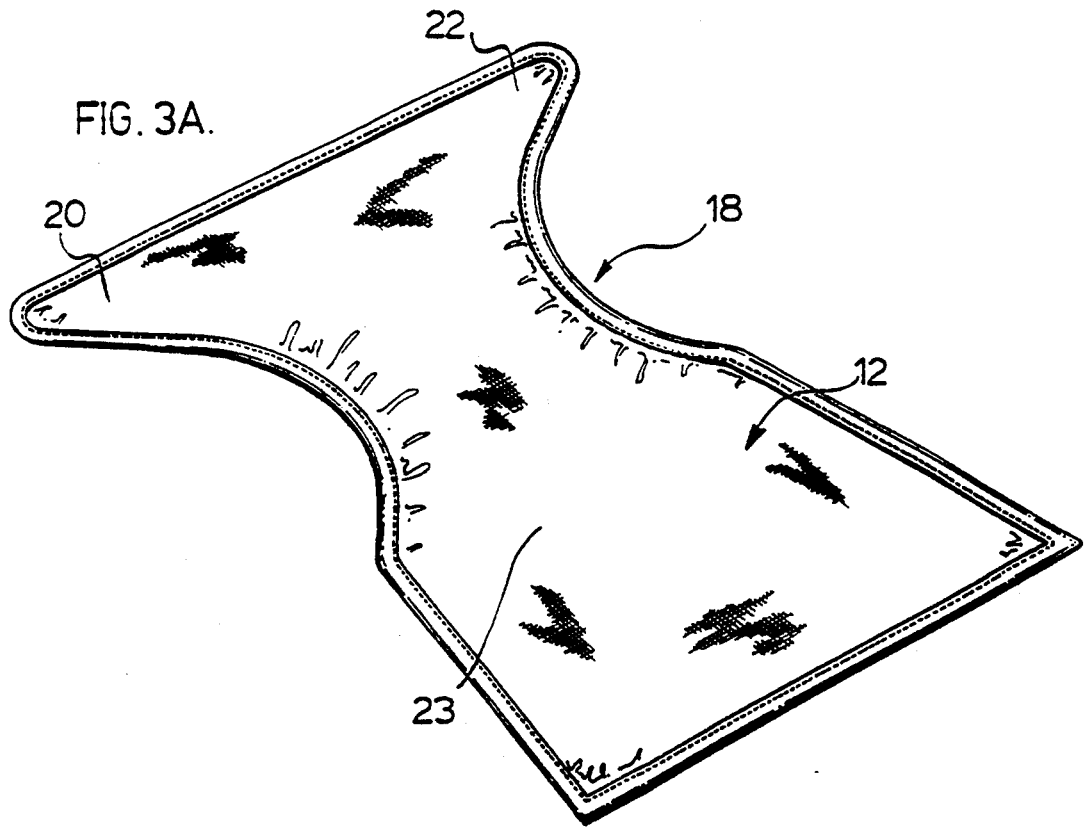
FIG. 3A.
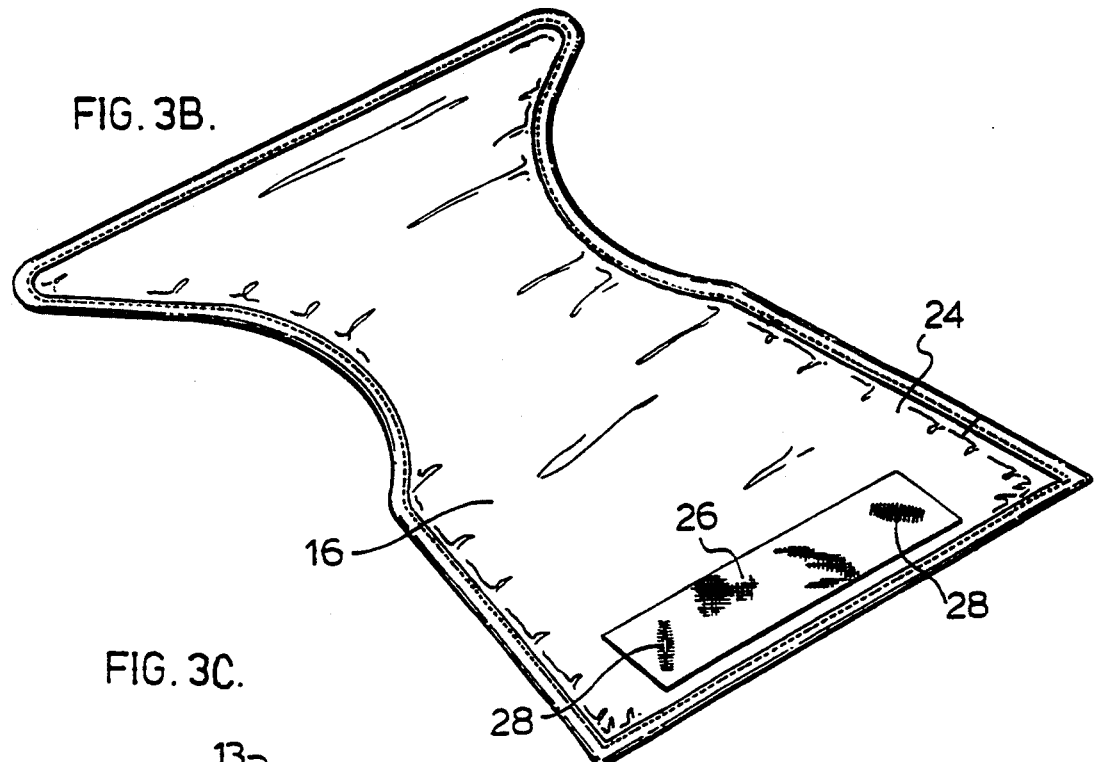
FIG. 3B.
FIG. 3C.
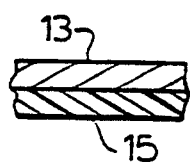

REUSABLE DIAPER

This application is a continuation-in-part of Ser. No. 07/650,543, filed Feb. 5, 1991, now U.S. Pat. No. 5,267,991.

FIELD OF INVENTION

This invention relates to a reusable incontinence pad. More particularly, it relates to a novel reusable incontinence pad, in a diaper form example, having improved fluid absorption, dispersion and retention characteristics.

BACKGROUND OF THE INVENTION

In recent years, the conventional cotton or flannel diapers have been replaced by disposable diapers. These disposable diapers not only avoid the problem of having to be washed after soiling, but many of the newer disposable diapers exhibited improved fluid adsorption and dispersion characteristics over the conventional cloth diaper.

Intense competition in the marketing of disposable diapers has resulted in a diaper product that not only has greater fluid absorbency and dispersion than earlier products but is also capable of holding the wetness within the interior of the diaper layers for prolonged periods of time so that the inner surface worn next to the skin continues to feel dry. Such "stay dry" diapers allow the wearer to go for longer periods between changes.

One drawback of disposable diapers is that they are not readily biodegradable. The increase in their popularity in recent years has resulted in an overload at garbage and landfill sites to the point where they contribute to serious environmental problems.

Disposable diapers or incontinence pads from hospital wards are treated as infectious wastes and must De disposed of at the special landfill sites set aside for such purposes, thereby adding to the critical space shortage at such sites. On the other hand, if the disposable diapers are incinerated, the combustion of the inner pulp layer or the impermeable layer may release dangerous toxins into the atmosphere.

It is estimated that approximately 85% of Canadian babies now wear disposable diapers. In the City of Toronto alone, this is a market of some 43 million disposable diapers per year. In addition to disposal problems. these diapers consume a large quantity of our natural resources. It is estimated that up to 1.8 trees per year are destroyed for each child who relies on disposable diapers throughout the child's training period. By using the diaper of the present invention instead of disposable diapers over a 2 ½ year period, a child would use approximately 108 reusable diapers as compared to some 7400 disposable diapers if such reusable diapers were used exclusively during this training period.

The applicant's reusable diaper has further ecological advantages in that at the end of its functional life, the diaper can be stripped apart and the viscose rayon fibres that constitute the median layer can be recycled to form up to 50% of a new median layer composition for such diapers.

Furthermore, the wetted reusable diaper does not have to be soaked in a diaper pail before laundering, as the absorbent median layer holds the liquid and its accompanying odour within the diaper. In the case of solid waste, the diaper can include a tissue liner which can be made of degradable fibrous tissue. This is laid on the interior layer of the diaper and can easily be separated and discharged into the sewer system. Alternatively, a liner of open weave synthetic fibres such as polyester can be used to retain the waste and this can be reused after removal from the diaper and rinsing out the solids.

While attempts are being made to produce biodegradable disposable diapers, such attempts have achieved only limited success. The disposable diaper components do not break down in the oxygen and sunlight starved environment of a landfill site. In view of these shortcomings, it is vital to provide an improved reusable diaper product.

Diapers of multilayered cotton or cotton and synthetic fabric blends show improved absorbency over the original cotton type diapers but tend to be thick and heavy. They also become soggy with every void. These thick multilayered cotton diapers also tend to take an unduly long time to dry after washing, which adds to power costs and down time for laundering. This is an important consideration in hospitals and commercial diaper services that have a large diaper turnaround.

Cotton reusable diapers must be presoaked before laundering in order to prevent the odours associated with a soiled diaper from permeating. Since the diapers have been soaking, they must be spun to remove the excess water prior to laundering.

Some cotton reusable diapers include a "stay dry liner" worn next to the skin so that fluid can pass through the liner and into the multilayered cotton portion. By passing the fluid through the fabric that contacts the wearer's skin, the wearer avoids the wet feeling that comes from a wetted cotton diaper. Although such linings feel dry to the touch, they do not absorb any fluid. Therefore if the cotton portion does not fully absorb the fluid the liner will not prevent the excess fluid from flowing back from the cotton portion to the wearer's skin. This effect is known as "wet back".

Impermeable pants may be worn on the outside of the multilayered cotton diaper to prevent any wetting of an outside garment that might be included on the wearer. This, of course, adds to the bulk of the diaper as well as its cost and may also require fasteners for holding the pant in place.

In view of these problems, it is imperative that a washable and reusable diaper be produced that has the comfort, appearance and absorption qualities comparable to those found in disposable diapers. The diaper of the present invention was found to be capable of being used for up to 250 washes as compared to the cotton diaper having a stay-dry liner which tends to mat and deform after about 40 washes.

Reusable diapers of the prior art may be tailored or form fitted, but generally are so designed that one size is made to fit all wearers, with the result that they often do not fit very well. Such reusable diapers are generally secured about the wearer using a fastening means such as pins, snaps or hook and loop fasteners such as Velro ®. Much time and effort is needed to fold and fasten such diapers with pins. Since snaps are anchored at specific points on the diaper, they do not allow adjustment for a custom fit.

Pins must be removed from the diaper prior to washing to prevent clogging of the washing machine and the rusting of the metal safety pins. The hooks and loops of Velro ® fasteners become clogged with lint during washing and the Velro ® fasteners may adhere to one another or to other diapers thereby balling and entangling the laundry load together. Hence, reusable diapers having Velro ® fasteners are unsuitable and inappropriate for hospital, institutional and commercial use.

Incontinence bed pads, which actually serve as open diapers on a bed, usually consist of cotton or polyester or blends thereof and require an impermeable sheet underneath. Again, these lack sufficient absorption to keep the bed patient dry when the patient's skin contacts the upper surface of the pad.

Adult type reusable incontinence pads and diapers usually comprise blended combinations of cotton, polyester and rayon. These are produced using a needlepunch method to prepare the absorbent layer. However, they have been found to lack sufficient absorbency to keep the voided fluid from contacting the wearer's skin. Such commercially available incontinence pads claim to be able to withstand up to 200 washes but have been tested in industrial wash cycles and found to be limited to about 75 wash cycles before the pads become unusable because of the impermeable layer begins breaking down or the stitching becomes damaged or the material becomes frayed.

SUMMARY OF INVENTION

It is therefore an object of one aspect of the present invention to provide a reusable pad having improved fluid absorption and dispersion characteristics, particularly useful as an incontinence pad.

It is an object of another aspect of the invention to provide a reusable pad having improved fluid retention characteristics, particularly useful as an incontinence pad.

It is an object of still another aspect of the invention to provide a reusable pad having odour retention characteristics, particularly useful as an incontinence pad.

These and other objects are achieved by means of a reusable incontinence pad comprising:
a) an interior layer for contact with the skin of a wearer, said layer being a soft hydrophobic web of polyester fibres;
b) a median layer consisting of non-woven webs of carded and cross-laid viscose rayon fibres, said fibres having a cross-section of substantially rigid multilimbed configuration, said webs being stitchbonded to form a cohesive layer of retained absorbency; and
c) an outer layer of substantially waterproof polyurethane film; said interior layer, median layer and outer layer being joined to form a pad of unitary construction.

It is another object of this invention to provide a novel web of viscose rayon fibres for use in a reusable incontinence pad or the like.

This object is achieved by means of a non-woven mat of absorbent material, said mat comprising:
webs of carded and cross-laid viscose rayon fibres having a cross-section of substantially rigid trilobal configuration and a water imbibition characteristic of 100 to 345 percent, being stitchbonded with polyester thread in rows spaced to provide approximately 2 to 10 rows per 2.54 cm (1.0 inch) of web with each of said rows having from 6 to 20 stitches per 2.54 cm (1.0 inch), said stitching thread being under medium tension whereby uniform absorption is retained throughout said mat.

It is still another object of this invention to provide a novel fastening means for a diaper which can be retained on the diaper during washing, is easy to fasten when folding the diaper onto a wearer and yet provide for custom folding for adjustment to the wearer's size.

This object is achieved by means of a fastening device comprising:
a) a fabric securing member including an internal portion for retaining on an outer surface of said diaper pad and a projecting portion extending therefrom;
b) a gripping member extending from said projecting portion and held in biased relationship against said internal portion;
c) a contacting surface between said gripping member and said internal portion for securing a portion of said diaper paid therebetween; and
d) finger contacting means on said gripping member for releasing said gripping member for contact with said internal portion.

DETAILED DESCRIPTION OF THE DRAWINGS

In the drawings which illustrate embodiments of the invention:

FIG. 3A is a plan view of one side of an incontinence pad of the present invention contoured for diaper use;

FIG. 3B is a plan view of the opposite side of the pad of FIG. 3A;

FIG. 3C illustrates the cross-sectional configuration of the outer layer shown in FIG. 3B;

DETAILED DESCRIPTION OF THE INVENTION

The incontinence pad or diaper of the present invention was found to have its unique absorption, dispersion and retention characteristics by virtue of the specific components of the three layers.

Figure 2:
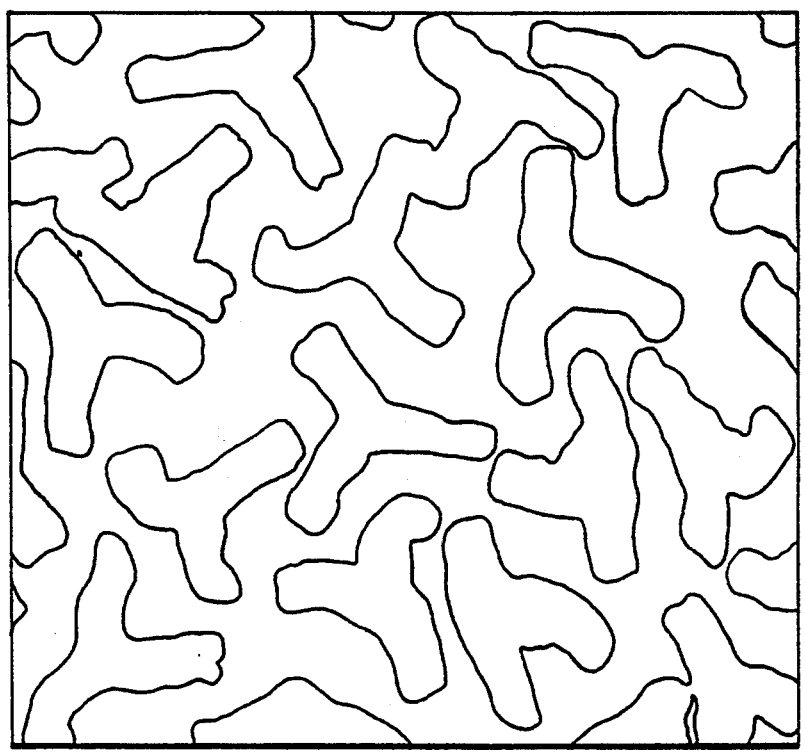
FIG. 2 is a cross-sectional photo-micrograph illustration of one embodiment of a viscose rayon fibre used in the invention.

The median layer that was found to be most desirable for a pad or diaper of this type consists of viscose rayon fibres having a multilimbed cross-sectional configuration which gives it superior bulk and absorbency. Viscose rayon fibres developed by Cortaulds Limited, as described in European Patent Application No. 301,874 and produced under the "GALAXY" brand are particularly good to achieve the fluffiness that is necessary in a non-woven web of this type. The trilobal fibres available under the "GALAXY I" brand was found to have a relatively even dispersion characteristic as well, so that fluid deposited in the center of the web is absorbed not only within the web itself but is dispersed toward the outer edges of the web in substantially even distribution. Examples of the cross-sectional configuration of the "GALAXY I" trilobal fibre is shown in FIG. 2.

The web of the median layer is produced by carding and crosslaying the viscose rayon fibres in layers to provide the desirable thickness. For general diaper use this preferred thickness is approximately 203.1 to 677.0 grams per square metre (6 to 20 oz. per sq. yd.) with the most preferred thickness being approximately 270 grams per square meter (8 oz. per sq. yd.). The web is maintained as a cohesive unit by stitchbonding by using a MAL1® or ARACHNI® stitchbonding machine. The webs of this invention were produced on a MALLYMO® machine made by Textina Inc.

Stitchbonding involves a machine which uses a row of needles to drive a binding thread through and back up the web as in a conventional sewing arrangement and in a manner well known in the art. The stitchbonding process and uses for fabrics made from stitchbonding have been described in U.S. Pat. No. 4,876,128. However, the stitchbonded fabrics disclosed therein are required to be bonded either chemically or thermally prior to being processed by the stitchbonding machines or are designed to be gathered to increase the insulation value of the fabric.

It was found that in order to maintain the absorbency and dispersion integrity of the viscose rayon web while insuring its cohesion, the stitchbonding was carried out using a polyester thread having a thickness of approximately 150 denier. It must be appreciated that some variation in the thread thickness can be accommodated. The stitchbonding was carried out using multiple needles to provide a series of substantially parallel stitch rows spaced apart to give approximately 2 to 10 rows per 2.54 cm (1.0 inch) with approximately 5 rows per 2.54 cm (1.0 inch) being the most preferable for diaper purposes. Each such row contains approximately 6 to 20 stitches per 2.54 cm (1.0 inch) with 12 stitches being the most preferred.

Using the MALLYMO® stitchbonding machine, the polyester thread is stitchbonded under a medium tension so that the viscose rayon fibre that is gripped by the thread is not bunched up and tightened in a manner that would interfere with uniform absorption and dispersion of the fluid over the whole web area. While some variation in thread tension is permitted, depending on the thickness of the web itself, such tension is usually determined visually by observing the fluffiness of the web after stitchbonding. If the resulting web is too matted, the tension of the thread should be reduced.

The water imbibition characteristic of these "GALAXY" multilimbed fibres make them particularly suitable for the applicant's absorption mat and for diapers and incontinence pad containing such mats. Various trilobal and multilobal viscose rayon fibres of this type were found to have a water imbibition characteristic of 100 to 345 percent.

Water imbibition was measured by taking a gram sample of the fibre and soaking it in water at a temperature at 20 degrees C. for 15 minutes, then subjecting it to a centrifugal force of 1000 grams for 5 minutes, weighing and drying the fibre for 2 ½ hours at 110 degrees C. and re-weighing it. The percent imbibition was determined by dividing the difference in weight between the wet and dry fibre by the weight of the dry fibre alone and multiplying by 100.

While the median layer of the present invention is considered unique in itself, the incontinence mat or diaper of the present invention which incorporates this median layer also includes additional elements that make the pad or diaper particularly suitable as a "stay dry" pad that can be worn over prolonged period without giving the wearer a wet or sticky feeling.

Figure 1:
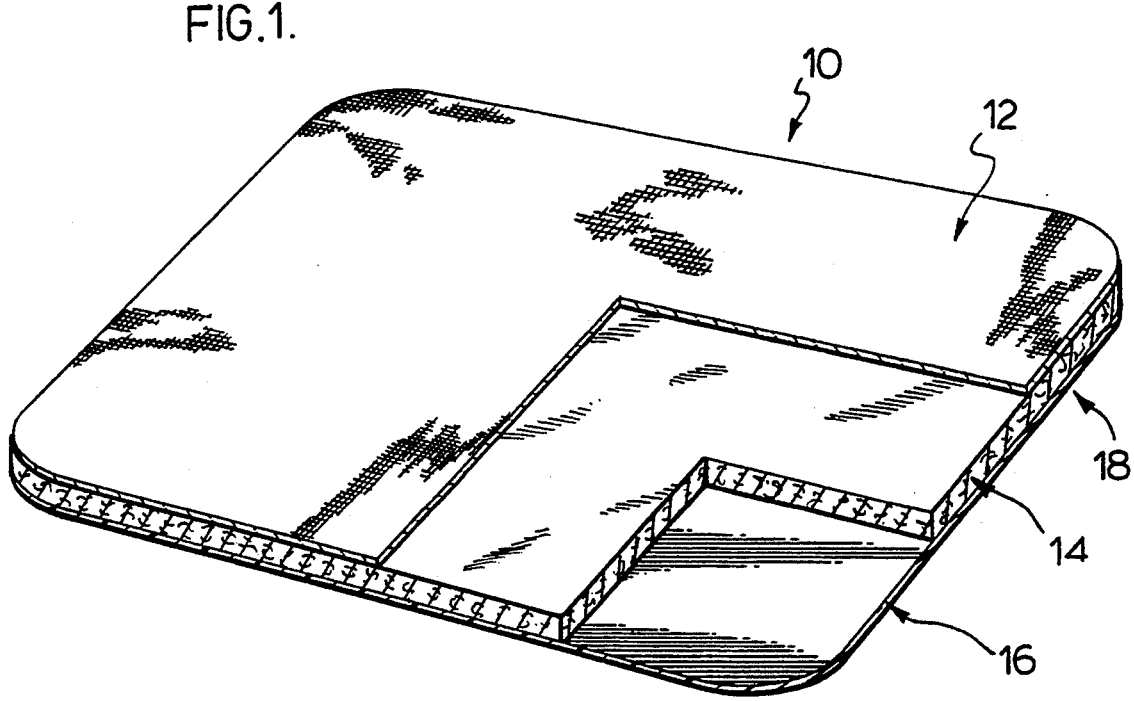
FIG. 1 is a top plan view of an incontinence pad of the present invention: showing one end section in cutaway illustration.

FIG. 1 shows an incontinence pad 10 with sections cut away illustrate the positioning of the three layers. The interior layer 12 or top layer, which is the layer that normally contacts the skin of the wearer, is laid immediately above the viscose rayon median layer. This interior layer 12 is a soft hydrophobic web of polyester fibres which has been warp knitted tricot stitched to give the desired porosity. The skin-contacting outer surface of this layer is napped finished by brushing to give a fibrous or padded texture that is comfortable to wear next to the skin.

When fluid waste from the wearer is discharged onto the interior surface of interior layer 12, the hydrophobic characteristic of the fibre prevents the fluid from collecting there. It quickly seeps through the porous stitching down into the median layer 14 where it is absorbed and dispersed. The wearer can continue to wear the diaper without discomfort, as such fluid would not usually return to the interior surface of interior layer 12 i.e, wet back, even when body weight is applied to a particular discharge area of the pad. When such fluid is passed into the median layer 14 it quickly and evenly disperses outwardly toward the various corners so that the viscose rayon median layer 14 can retain a considerable amount of fluid without sogginess.

Since the fluid is absorbed by the median layer 14, it will also retain the odours normally associated with a wetted diaper.

To give a thick and comfortable appearance to the inner surface of interior layer 12, it was found most desirable that this polyester fibre be knitted to a thickness of approximately 101.6 to 169.3 grams per square metre (3 to 5 oz. per sq. yd.), with the preferable thickness being 148.9 grams per square metre (4.4 oz. per sq. yd.). Greater thickness would provide the same desirable absorption, but would make the diaper uncomfortably thick. Such greater thickness can be used in incontinence pads but would add to the cost.

An outer layer 16 of the pad or diaper provides further waterproofing, particularly for any outer clothing that might be worn over the diaper. This outer layer 16 is mounted over the bottom or "downstream" surface of the viscose rayon median layer 14 and includes a polyurethane film that contacts the median layer 14 and prevents absorbed fluid from passing through.

While the pad or diaper of this invention would be functional with a polyurethane outer film, this would give the appearance of a plastic pants that would not be as comfortable as a textured outside surface. For this reason the outer layer preferably includes an outside fibrous surface so that the entire pad or diaper gives the thickness and rich appearance of a textile fabric on both sides.

This rich textile appearance on the outer layer is achieved by means of a web of polyester fibre which is warp knit tricot stitched. The polyurethane film 15 is then pre-stretched and bonded to the knitted polyester fibre 13 (see FIG. 3C). This pre-stretching gives the outer layer a thick bumpy appearance as well as additional strength once the polyurethane film is relaxed. The thickness of the polyester fibre portion of the outer layer however, does not need to be as thick as the polyester fibre of the inner layer of the pad and is normally between 67.7 to 135.4 grams per square metre (2.0 and 4.0 oz. per sq. yd.), with the preferable thickness being 74.5 grams per square metre (2.2 oz. per sq. yd.).

The three layer components are stacked together to form the pad or diaper and are stitched together only around the periphery of their mated edges and a finishing edge 18 of woven polyester fibre is usually sewn around the parameter to give the pad a smooth finish. It is noted that the interior layer 12 is otherwise unperforated by a stitching process.

Diapers and pads of the present invention were found to be washable and ready for reuse up to 250 times before the median layer 14 loses its absorption and dispersion characteristics.

FIG. 3A shows a pad of this invention formed into a contoured diaper. In this Figure, the interior layer 12 which is worn next to the skin. is shown uppermost. The pad is edge trimmed with a finishing edge 18 and is contoured in a substantially hourglass shape with a relatively narrow center area for fitting the diaper around the crotch of the wearer. The pad is widened at its forward end to provide a pair of oppositely extending wing edges 20 and 22 for easy folding and fastening around the trunk of the wearer. The edge of the crotch area may also be gathered to provide a better fit around the leg of the wearer.

In FIG. 3B the outer layer 16 is shown uppermost. It can be seen that the relatively narrow end 29 of the diaper opposite the extending wing edges 20 and 22 includes a buttonhole fabric 26 with a pair of buttonholes 28 for fastening releasable fastening members 100 in a manner to be described below.

Figure 4:
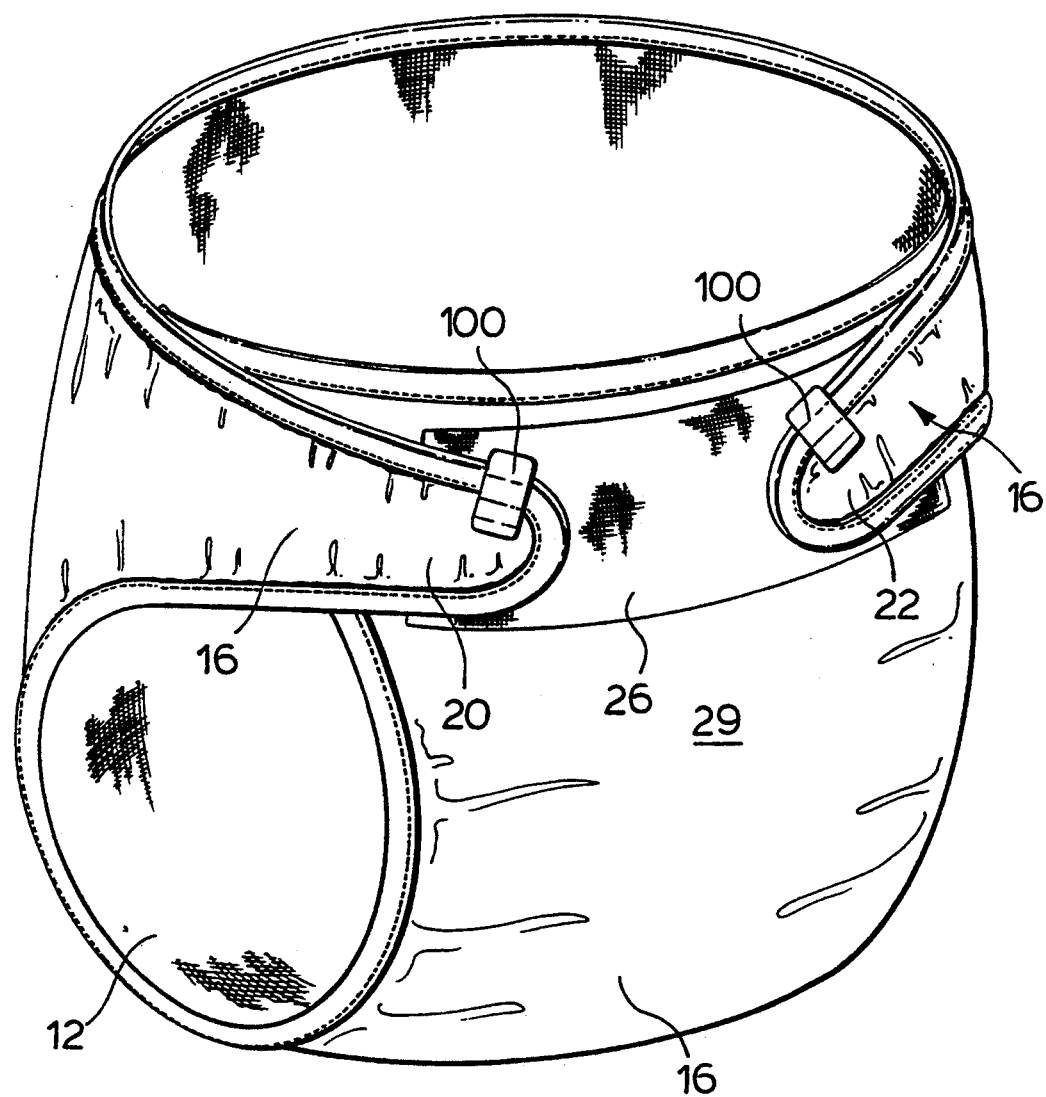
FIG. 4 is a perspective illustration of a contoured diaper as folded and fastened around the trunk of a wearer.

FIG. 4 shows the diaper folded and fastened as if contoured around the trunk of a wearer. The outer layer 16 is shown with the narrow end 29 of the diaper drawn forward of the crotch and positioned to cover the abdominal area of the wearer. With the opposite end of the diaper covering the rear end of the wearer, the oppositely extending wing edges 20 and 22 can be seen to extend sufficiently forward so that their leading ends overlie one of the buttonholes 28. Each of the buttonholes 28 secures a fastening member 100, such as the type described below. With one portion of the fastening member anchored into a buttonhole 28, the releasable securing means on the fastening member grips the leading edge of the respective extending wing edges 20 and 22. If the fastener member 100 is a type capable of gripping the fabric of the extending wing edges 20 and 22 anywhere along its length, the wing edges 20 and 22 can be tugged forward so that the diaper wraps snugly around the wearer before the fastener member 100 is engaged.

The diaper as shown in FIG. 3A, may be used with a mesh liner 23 which is inserted onto the inside layer 12. The mesh liner 23 is used to collect solid excrement. The liner together with the excrement can be flushed down the toilet for disposal in the sewage system. The liner is preferably made of a biodegradable fibrous mesh so that both the excrement and the liner can be flushed into the sewage system. However, the liner could be made of a polyester mesh which could be washed and reused.

Figure 5A:
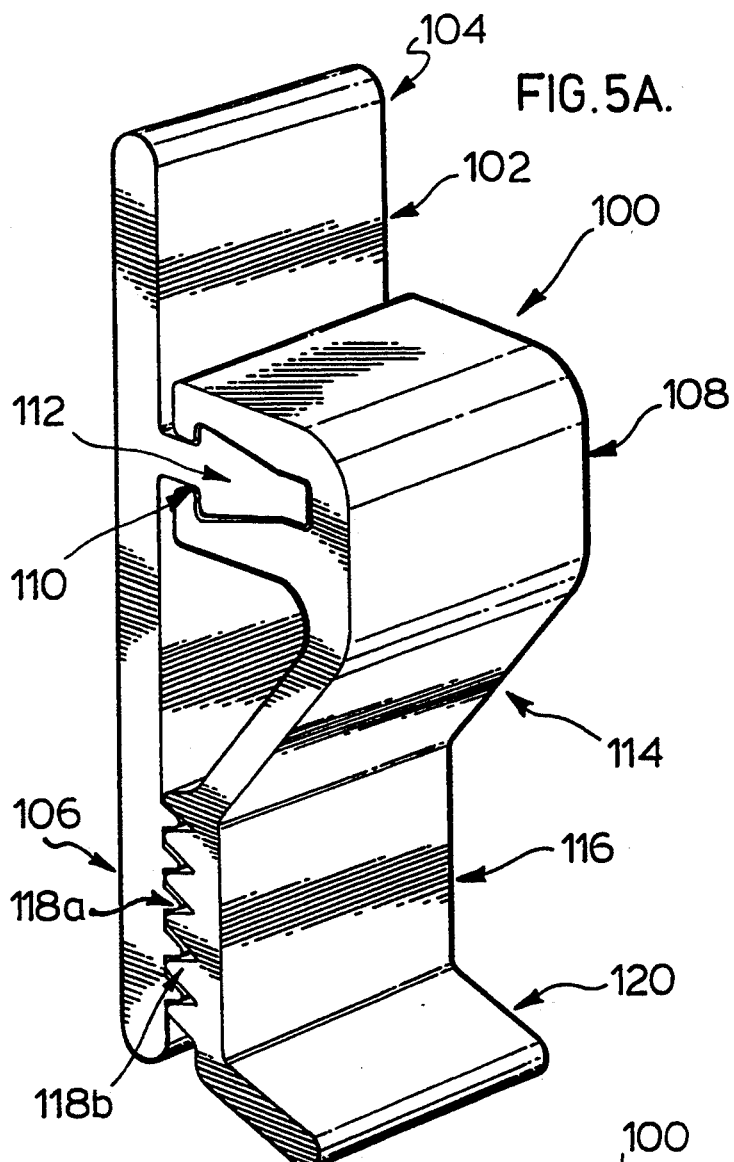
FIG. 5A is a perspective view of one embodiment of the fastening device of the present invention.

One embodiment of the novel fastening device of the present invention is shown at 100 in FIG. 5A and comprises a pair of mating components of polyurethane or the like, which may be produced by extrusion. The fabric securing member 102 is fitted into buttonhole 28 by securing the upper and lower extremities 104 and 106 into buttonhole 28. The clip member 108 includes a securing jaw 110 which is clamped on in mating engagement with arm 112 of securing member 102. In this embodiment the two components 102 and 108 are so designed to be secured in permanent engagement. Securing member 102 and clip member 108 can comprise an integral unit but, as is demonstrated in another embodiment, it may be convenient for moulding purposes to produce these members separately.

Clip 108 includes a biased arm 114 which extends downwardly from the securing jaw portion to a gripping plate 116 and impinges this plate against lower extremity 106 of fabric member 102. It can be seen that plate 116 and extremity 106 includes interlocking ridges 118. It must be appreciated that when fabric securing member 102 is fitted onto the fabric buttonhole, ridges 118a are inside the buttonhole fabric material, so ridges 118a and 118b do not actually interlock, but provide a degree of intermeshing through the buttonhole material. An engaging lip 120 extends from gripping plate 116 for lifting the plate free from engagement against lower extremity 106.

When the fastening device is mounted onto the diaper and the diaper folded around the child as shown in FIG. 4, extending wing edges 20 and 22 are clipped into place by lifting engaging lip 120 and slipping the extending wing edges 20 and 22 in between plate 116 and the buttonhole fabric material 26 that is immediately forward of ridges 118a. There is sufficient traction between ridges 118b and the contour of the buttonhole fabric 26 to hold this end portion in place when plate 116 is released to its engaging position.

The clip is so designed that while extending wing edges 20 and 22 are easily engaged and disengage by an adult, a young child would not have the hand coordination necessary for lifting the gripping plate free of its mounting and removing the fold over ends from the interlocking ridges.

Further, buttonhole fabric 26 may be stitched about the area of buttonholes 28 such that the contour of the stitching matches the outline of fabric securing member 102. Upon insertion into buttonhole 28, fastener member 100 fits snugly and securely onto the diaper.

Figure 5B:
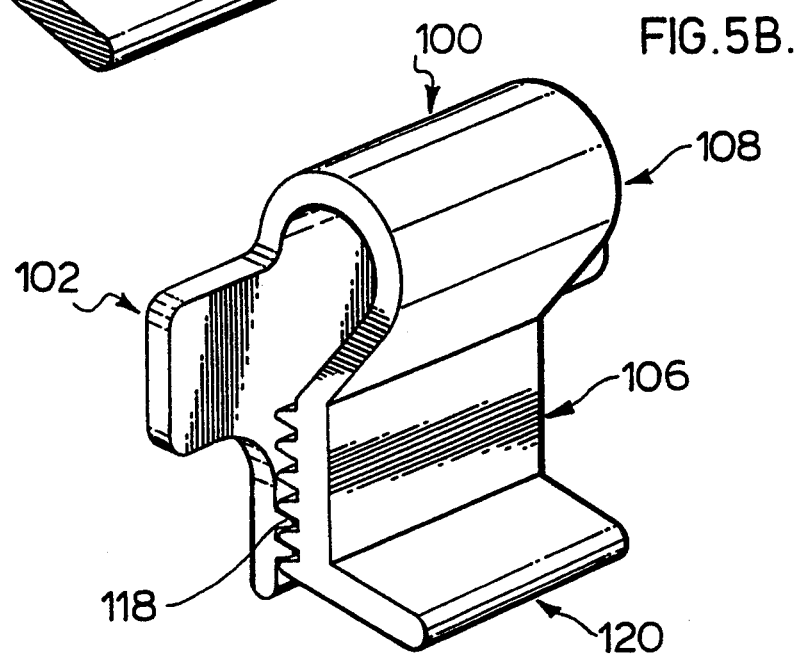
FIG. 5B is a perspective view of another embodiment of the fastening device.

In FIG. 5B another embodiment of the fastening device 100 is shown. This is basically similar to the embodiment shown in FIG. 5A but the fabric securing member 102 and clip member 108 constitute an integral unit that is made preferably by separate casting or injection moulding. Again with the fabric securing member fitted into a buttonhole 128 or otherwise sewn into the outer layer of the diaper, extension wing edges 20 and 22 of the diaper can be wedged in place between ridges 118a and 118b in the manner described above.

Although clip 108 is fitted snugly onto the diaper, they may be removed once the diaper has exceeded its usable lifespan. The used clips may be fitted onto new diapers thereby increasing the recyclability of the invention.

In use, the diaper is wrapped around the wearer in a conventional fashion. Once the diaper has been soiled, it may be exchanged for a clean diaper. The soiled liner is disposed of into the sewage system and the soiled diaper is placed in a diaper hamper or basket. Once a sufficient number of soiled diapers has accumulated, they may be laundered and dried for reuse in a conventional fashion.

Once the diaper has exceeded its useful lifespan and several components of the diaper may be removed from the diaper for recycling in new diapers. The rayon fibres of the median layer 14 may be removed and reused. Further, the clips 108 may also be reused.

In an alternate embodiment, the multilimbed fibre may be manufactured as a blend of the multilimbed fibre and a polyester fibre to improve the strength of the resulting fibre. It is possible to use between 5% to 40% polyester fibre in this invention. Although increases in the amount of polyester used in the fibre results in a stronger fibre able to withstand a greater number of washes, there will also be a reduction in the absorbency characteristics of the pad. The preferred composition is 80% of the trilobal fibre and 20% polyester.

The reusable pad as described herein may have other uses for absorbing fluid such a surgical sponge or a feminine hygiene pad. The stitchbonded mat by itself could be used as a surgical sponge. The stitchbonded mat could be sandwiched between layers of a hydrophobic web of polyester fibres and contoured for use as a feminine hygiene pad.

Figure 6:
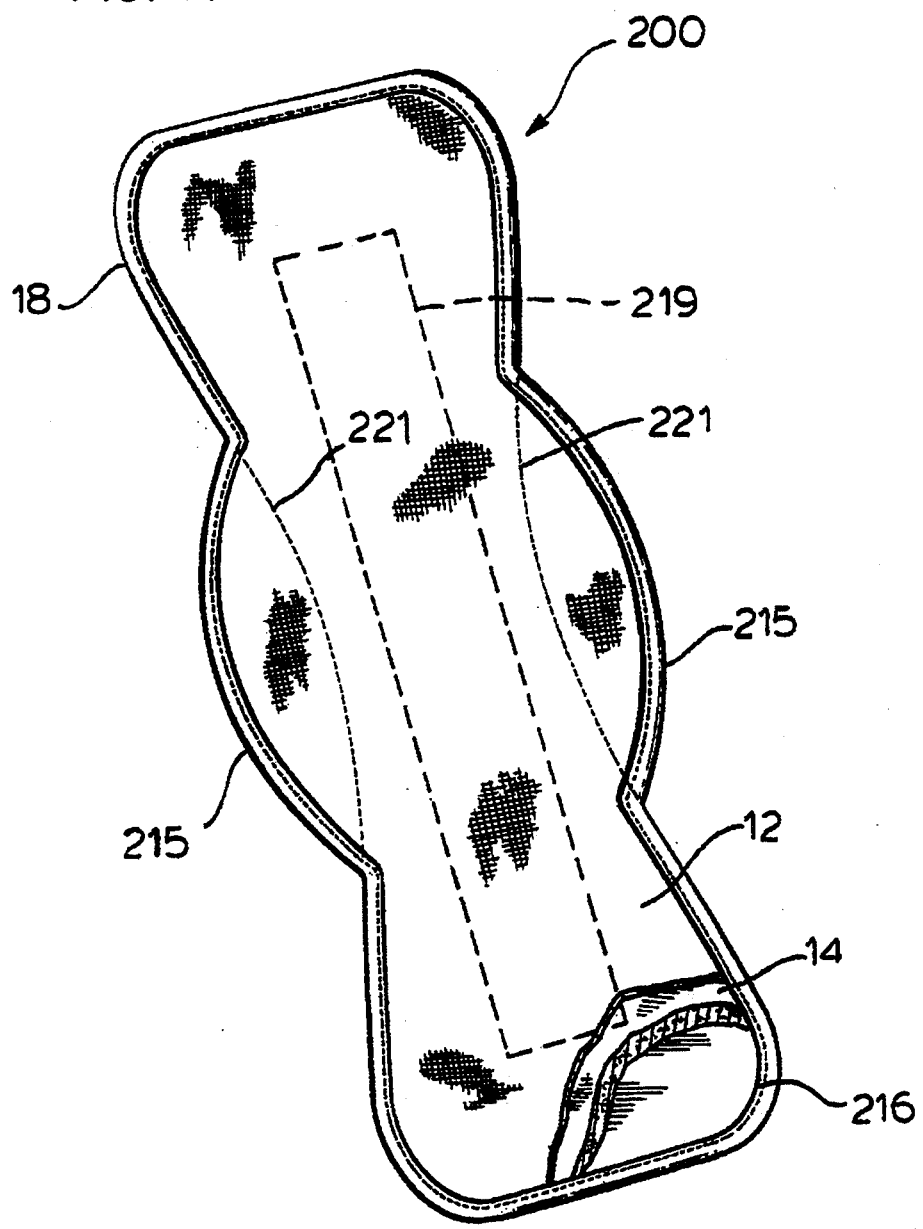
FIG. 6 is a perspective view of another embodiment of the pad of the present invention for use as a feminine hygiene pad, showing one end section in cut-away illustration.

As illustrated in FIG. 6, a pad 200 is generally in an hourglass shape, which is common for pads of this type. Optionally, the pad can have wings 215 for wrapping around the wearer's undergarment, providing leak protection.

The pad 200 has a similar construction as the pad 10. The interior layer 12 or top layer, which is the layer that normally contacts the skin of the wearer, is laid immediately above the viscose rayon median layer 14. This interior layer 12 is a soft hydrophobic web of polyester fibres which has been warp knitted tricot stitched to give the desired porosity.

An outer layer 216 of the pad 200 provides further waterproofing, particularly for the undergarments that are worn over the pad. This outer layer 216 is mounted over the bottom or "downstream" surface of the viscose rayon median layer 14 and includes a polyurethane film or other water impermeable material that contacts the median layer 14 and prevents absorbed fluids from passing through.

The fluid receiving area of the pad 200 is generally not perforated by a stitching process. However, a row of stitching 221 may be used to provide a folding line for folding the wings about an undergarment. Optionally, wings 215 may have a medium layer 14 separate from the medium layer of the pad 200 and in some instances, the medium layer may be omitted.

In use, the pad 200 has a fastening device for fastening the pad 200 to the wearer's undergarment. The fastening device could be of any known variety, including a two-sided tape. The tape 219 is attached to the outer surface of layer 216 and then attached to the undergarment. If the wings are used, the wings are wrapped about the crotch region of the undergarment. After use, the tape 219 is disposed and the pad washed for future use.

Although the disclosure describes and illustrates preferred embodiments of the invention, it is to be understood that the invention is not limited to these particular embodiments. Many variations and modifications will now occur to those skilled in the art. For a definition of the invention, reference is to be made to the appended claims.

We claim:

1. A washable and reusable mat for the absorption, dispersion and retention of a liquid, said mat comprising a plurality of non-woven layers of carded and cross-laid viscose rayon fibres having a cross-section of substantially rigid multi-limbed configuration, said layers being stitchbonded together into a cohesive web, said layers stitchbonded with a thread under medium tension to stabilize and maintain the web whereby the fibres that are gripped by the thread are not bunched up and tightened in a manner that would interfere with uniform absorption and dispersion of the fluid throughout said web after repeated washings.

2. A washable and reusable mat as claimed in claim 1 wherein the viscose rayon fibres are of a trilobal configuration and have a water imbibition characteristic of from 100 to 345 percent.

3. A washable and reusable mat as claimed in claim 2 wherein the layers are stitchbonded with polyester thread in rows approximately 2 to 10 rows per inch, each of said rows having from 6 to 20 stitches per inch.

4. A washable and reusable mat as claimed in claim 1 in combination with:
   a) an interior layer of hydrophobic material presenting a receiving surface, said web adjacent the interior layer opposite the receiving surface:
   b) an outer layer of substantially waterproof polyurethane film adjacent the web;
   said interior layer, mat and outer layer being joined only along the outer edges thereof to form a pad of unitary construction.

5. A washable and reusable mat as claimed in claim 4, wherein the viscose rayon fibres of said web are of trilobal configuration and have a water imbibition characteristic of from 100 to 345 percent.

6. A washable and reusable mat as claimed in claim 5 wherein said layers of viscose rayon fibres are stitchbonded with polyester thread along a series of rows spaced approximately 2 to 10 rows per inch with each of said rows having from 6 to 20 stitches per inch.

7. A washable and reusable mat as claimed in claim 6 wherein said interior layer is warp knit tricot stitched, and said receiving surface is nap finished.

8. A washable and reusable mat as claimed in claim 7, wherein said outer layer comprises a first lamina of pre-stretched film of polyurethane bonded to a second lamina comprising a layer of warp knit tricot stitched polyester fibres and in which said first lamina is positioned adjacent said web.

9. A washable and reusable mat as claimed in claim 8, wherein the interior layer has a thickness of from 2.0 to 5.0 ounces per square yard, said median layer has a thickness of from 6.0 to 20.0 ounces per square yard, and said second lamina has a thickness of from 2.0 to 4.0 ounces per square yard.

10. A washable and reusable mat as claimed in claim 9 wherein said pad is contoured in an hourglass shape for wearing as a diaper and has a fastener device for securing said pad about a wearer.

11. A washable and reusable mat as claimed in claim 10 in combination with a mesh liner for receiving and disposing solid excrement, said mesh liner is placed adjacent said receiving surface of said interior layer, and said liner is biodegradable and is flushable.

12. A washable and reusable feminine hygiene pad for the absorption, dispersion and retention of liquids, said pad comprising:
   a) an interior layer of hydrophobic material presenting a receiving surface:
   b) a median layer adjacent the interior layer opposite the receiving surface comprising carded and cross-laid layers of unbonded viscose rayon fibres, said fibres having a cross-section of substantially rigid multi-limbed configuration, the layers of rayon fibres stitchbonded with a thread under medium tension to stabilize and maintain the layers of rayon fibres in a cohesive web whereby the fibres that are gripped by the thread are not bunched up and tightened in a manner that would interfere with uniform absorption and dispersion of the fluid throughout the web;

c) an outer layer of substantially waterproof polyurethane film adjacent the median layer;

said interior layer, median layer and outer layer being joined only along the outer edges thereof to form a pad of unitary construction.

13. A feminine hygiene pad as claimed in claim 12 wherein said pad has an hourglass shape and a fastening means for fastening said pad to an undergarment.

14. A feminine hygiene pad as claimed in claim 13, wherein the viscose rayon fibres of said median layer are of trilobal configuration and have a water imbibition characteristic of from 100 to 345 percent.

15. A feminine hygiene pad as claimed in claim 14 wherein said layers of viscose rayon fibres are stitch-bonded with polyester thread along a series of rows spaced approximately 2 to 10 rows per inch with each of said rows having from 6 to 20 stitches per inch.

16. A feminine hygiene pad as claimed in claim 15 wherein said median layer has a thickness of from 6.0 to 20.0 ounces per square yard and said interior layer has a thickness of from 2.0 to 5.0 ounces per square yard.

17. A feminine hygiene pad as claimed in claim 16 wherein said interior layer is warp knit tricot stitched, and said receiving surface is nap finished.

18. A feminine hygiene pad as claimed in claim 17 wherein said pad further includes wings for wrapping about a crotch region of the undergarment.

19. A feminine hygiene pad as claimed in claim 18, wherein the viscose rayon fibres includes recycled viscose rayon fibres.

20. A feminine hygiene pad as claimed in claim 19, wherein viscose rayon fibres are blended with between 5% and 40% polyester fibres.

* * * * *